US006627221B2

(12) United States Patent
Gabel et al.

(10) Patent No.: US 6,627,221 B2
(45) Date of Patent: Sep. 30, 2003

(54) PHARMACEUTICAL COMPOSITION CONTAINING DIPHOSPHONIC ACID OR SALT THEREOF

(75) Inventors: Rolf-Dieter Gabel, Schwetzingen (DE); Walter Preis, Neustadt (DE); Heinrich Woog, Laudenbach (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/909,727

(22) Filed: Jul. 20, 2001

(65) Prior Publication Data

US 2002/0006441 A1 Jan. 17, 2002

Related U.S. Application Data

(62) Division of application No. 09/413,990, filed on Oct. 7, 1999.

(30) Foreign Application Priority Data

Oct. 9, 1998 (EP) .............................. 98119102

(51) Int. Cl.[7] .............................. A61K 9/20; A61K 9/48; A61K 9/28; A61K 9/14; A61K 31/66
(52) U.S. Cl. ........................ 424/464; 424/465; 424/489; 424/466; 424/451; 424/452; 424/441; 514/108
(58) Field of Search ................. 424/489, 464, 424/465, 466, 451, 452, 441; 514/960, 108

(56) References Cited

U.S. PATENT DOCUMENTS

| 4,624,947 | A | | 11/1986 | Blum et al. |
|---|---|---|---|---|
| 4,711,880 | A | | 12/1987 | Stahl et al. |
| 4,798,725 | A | | 1/1989 | Patel |
| 4,859,472 | A | * | 8/1989 | Demmer et al. |
| 4,927,814 | A | | 5/1990 | Gall et al. |
| 4,939,130 | A | | 7/1990 | Jaeggi et al. |
| 4,980,171 | A | | 12/1990 | Fels et al. |
| 5,358,941 | A | | 10/1994 | Bechard et al. |
| 5,525,354 | A | | 6/1996 | Posti et al. |
| 5,622,721 | A | | 4/1997 | Dansereau et al. |
| 5,662,918 | A | | 9/1997 | Winter et al. |
| 5,681,590 | A | | 10/1997 | Bechard et al. |
| 5,882,656 | A | | 3/1999 | Bechard et al. |

FOREIGN PATENT DOCUMENTS

| EP | 0 275 468 | 7/1988 |
|---|---|---|
| EP | 0 583 470 | 2/1994 |
| EP | 0 625 355 | 11/1994 |
| WO | WO 93/09785 | 5/1993 |
| WO | WO 93/21907 | 11/1993 |
| WO | WO 94/05297 | 3/1994 |
| WO | WO 94/12200 | 6/1994 |
| WO | WO 95/29679 | 11/1995 |
| WO | WO 96/41618 | 12/1996 |
| WO | WO 97/39755 | 10/1997 |
| WO | WO 00/21540 | 4/2000 |
| WO | WO 00/21541 | 4/2000 |

OTHER PUBLICATIONS

English language Abstract for Document B1.
English language Abstract for Document B2.
Remington's Pharmaceutical Sciences, Mack Printing Company, Easton, PA pp. 1604–1615 (1985).
Abstract corresponding to WO 97/39755.

\* cited by examiner

*Primary Examiner*—Thurman K. Page
*Assistant Examiner*—Amy E Pulliam
(74) *Attorney, Agent, or Firm*—George W. Johnston; Patricia S. Rocha-Tramaloni; Bernard Lau

(57) ABSTRACT

The invention relates to a solid pharmaceutical form of administration containing a diphosphonic acid or a physiologically compatible salt thereof as the active substance, wherein the active substance is present in granulate form, optionally together with pharmaceutical adjuvants in the inner phase, and the outer phase contains a lubricant in the form of less than 5% by weight of stearic acid relative to the total weight of the form of administration.

4 Claims, No Drawings

PHARMACEUTICAL COMPOSITION CONTAINING DIPHOSPHONIC ACID OR SALT THEREOF

This application is a divisional application of U.S. application Ser. No. 09/413,990, filed Oct. 7, 1999.

BACKGROUND OF THE INVENTION

The invention relates to a solid pharmaceutical form of administration containing a diphosphonic acid, a physiologically compatible salt or hydrate thereof as the active substance and stearic acid as lubricant in the outer phase. The invention also relates to a process for preparing the form of administration.

Pharmaceutical forms of administration of diphosphonic acids are known for treatment of calcium metabolism diseases. Drugs containing these active substances are used for treating hypercalcaemia and also for treating tumour osteolysis resulting from bone metastases. They can also be successfully used for treatment of osteoporosis and resulting pain.

Since the active substances for treating diseases of this kind frequently have to be administered over a long period, oral application is very advantageous since it is usually more acceptable to the patient.

Oral forms of administration are known in the case of some diphosphonic acids and salts thereof. For example EP-B 0 275 468, EP-B 0 625 355 (both Boehringer Mannheim) and WO 93/21907 (Leiras Oy) disclose pharmaceutical preparations containing clodronic acid (dichloromethylene diphosphonic acid) or salts thereof. WO 93/09785 (Procter & Gamble Pharmaceuticals) discloses oral forms of administration of risedronate (the salt of 3-pyridyl-1-hydroxyethylidene-1,1-diphosphonic acid). WO 93/21907 and WO 93/09785 describe oral forms of administration provided with a coating which dissolves only at pH above 5 or 5.5. The aim is to ensure that the forms of administration travel through the stomach and the active principle is released only in the intestinal tract.

The solid forms of administration of diphosphonic acids or salts thereof described in the prior art contain the active substance and selected pharmaceutical adjuvants, with which the active principle must be compatible, in the inner phase and selected pharmaceutical adjuvants in the outer phase, more particularly for ensuring that the preparation can be easily processed in a capsule-filling machine or tablet press. For example EP-B 0 275 468 describes clodronate-containing drugs with a high proportion of 80–95% active substance, a filler content of 2–10% and a lubricant content of 0–5% in the granulate, to which is added an outer phase in the form of a lubricant, preferably magnesium stearate and talcum, in a proportion of 1–5%.

During the development of a capsule or tablet or other solid form of administration, special attention is usually paid to the adjuvants in the outer phase.

The selection and proportion of a suitable lubricant in the outer phase is particularly important, since it has great influence on the physical properties of the forms of administration under development. The choice and proportion determine whether the substance filling the capsule or tablet can be processed without difficulty on a suitable machine over a prolonged period or whether the tablets stick to the compression moulding dies in the machine. Sufficient lubricant must therefore be added to the outer phase. If however the proportion of lubricant is too high, there may be other adverse effects. For example the granulate may become so water-repellent that the resulting drug disintegrates only slowly and the desired dissolution rate (practically complete release of the active substance after 30 minutes) is not reached.

The following known lubricants can be used in the outer phase: magnesium stearate, calcium stearate, talcum, sodium stearyl fumarate, macrogol or hydrogenated esters of fatty acids with glycerine and stearic acid.

For example in EP-B 0 275 468, which describes oral forms of administration for clodronate, magnesium stearate and talcum are together used as a lubricant in the outer phase. EP-B 0 625 355 (Boehringer Mannheim GmbH) discloses magnesium stearate as the only lubricant in the outer phase of clodronate forms of administration. WO 93/21907 (Leiras Oy, clodronate) Example 1, describes the use of talcum and magnesium stearate as a lubricant in the outer phase and stearic acid as a lubricant in the inner phase. WO 93/09785 (Procter & Gamble, risedronate) Example 3, discloses stearic acid lubricant in a proportion of 5.8% by weight relative to the tablet core.

It has been found, however, that particularly when the proportions of active substance are low, the lubricant or the concentrations thereof are not optimum, since dissolution rates of 85% after 30 minutes, indicating uniform and almost complete release of the active substance, are not obtained or else the dissolution rates fall rapidly after stress through heating above room temperature.

SUMMARY OF THE INVENTION

The object of the invention therefore is to develop a pharmaceutical form for administration as a unit dose, i.e., a pharmaceutical form of administration in which the active substances are diphosphonic acids or physiologically compatible salts thereof and which is stable enough for the active substance to be released uniformly and almost completely within 30 minutes and for no reduction in the rate of dissolution to occur even after temperature stress. This should apply both to high and low contents of active substance in the form of administration.

Surprisingly it has been found that solid forms of administration containing less than 5% by weight of stearic acid lubricant in the outer phase, relative to the total weight of the form of administration, e.g. 0.1 to 4.9% by weight, have dissolution rates of at least 85% after 30 minutes, and the rates do not change even after weeks of exposure to temperatures of 40–50° C. This applies both to low and to high contents of active substance in the form of administration.

Less than 5% by weight stearic acid in the outer phase, relative to the total weight of the form of administration, results on the one hand in a sufficient lubricant effect, so that the tablet or capsule filler does not stick to the processing machines, and on the other hand the granulated active substance does not become water-repellent.

This aspect of the invention therefore relates to solid pharmaceutical dosage forms in which the active substance is a diphosphonic acid or a physiologically compatible salt thereof, wherein the active substance in granulate form, optionally together with pharmaceutical adjuvants, is present in the inner phase and the outer phase contains a lubricant in the form of stearic acid in proportions of less than 5% by weight relative to the total weight of the form of administration.

DETAILED DESCRIPTION OF THE INVENTION

In accordance with the present invention, the outer phase of the pharmaceutical form of administration contains a lubricant in the form of stearic acid in proportions of less than 5% by weight relative to the total weight of the form of administration. Preferably, the form of administration contains stearic acid in a proportion of 0.1 to 3%, particularly 0.9 to 3% by weight, relative to the total weight of the form of administration. Particularly, preferably stearic acid is added in a proportion of 1.5 to 2.7% by weight relative to the total weight of the form of administration, in which case the rate of release will be at least 90% (determined by the Paddle method after the USP).

The granulated active substance can contain pharmaceutically acceptable adjuvants and/or additives such as lactose, starch, glucose, mannitol, microcrystalline cellulose, hydroxypropyl methyl cellulose or other substances known for this purpose in the art.

The form of administration according to the invention can also contain other pharmaceutical adjuvants in the outer phase, more particularly a disintegrating agent, all known disintegrating agents being usable. More particularly cross-linked polyvinyl pyrrolidone (Crospovidone USPNF) is a preferred disintegrating agent for the purposes of the invention.

The following bisphosphonates are active substances which can be used according to the invention in the form of free acids or pharmaceutically compatible salts or hydrates, particularly sodium salts:

(4-amino-1-hydroxybutylidene)bis-phosphonate (alendronate), (Dichloromethylene)bis-phosphonate (clodronate), [1-hydroxy-3-(1-pyrrolidinyl)-propylidene] bis-phosphonate (EB-1053), (1-hydroxyethylidene)bis-phosphonate (etidronate), [1-hydroxy-3-(methyl pentyl amino)propylidene]bis-phosphonate (ibandronate),

[Cycloheptylamino)-methylene]bis-phosphonate (incadronate), (6-amino-1-hydroxyhexylidene)bis-phosphonate (neridronate), [3-(dimethylamino)-1-hydroxypropylidene]bis-phosphonate (olpadronate), (3-amino-1-hydroxypropylidene)bis-phosphonate (pamidronate), [1-hydroxy-2-(3-pyridinyl)ethylene]bis-phosphonate (risedronate), [[(4-chlorophenyl)thiol]-methylene]bis-phosphonate (tiludronate), [1-hydroxy-2-imidazo-(1,2-a)pyridin-3-yl ethylidene]bis-phosphonate (YH 529),

[1-hydroxy-2-(1H-imidazol-1-yl)ethylidene]bis-phosphonate (zoledronate).

Ibandronate, etidronate, clodronate, risedronate, pamidronate or alendronate or free acids thereof are preferred active substances according to the invention.

These substances and production thereof are known and described e.g. in the following references: U.S. Pat. No. 4,705,651 (Alendronate), U.S. Pat. No. 4,927,814 (Ibandronate), U.S. Pat. Nos. 3,468,935, 3,400,147, 3,475,486 (Etidronate), O. T. Quimby et al., J. Org. Chem. 32, 4111 (1967) (Clodronate), U.S. Pat. No. 4,505,321 (Risedronate) and U.S. Pat. Nos. 4,134,969 and 3,962,432 (Pamidronate).

The proportion of active substance in the form of administration according to the invention can be up to 95% by weight relative to the total weight of the form of administration. Active substance contents of 0.2–30% by weight, relative to the total weight of the form of administration, are particularly preferred. The method according to the invention can particularly preferably be used to make oral forms of administration containing 0.25–100 mg of active substance per unit dose, particularly up to 50 mg per unit dose. The term "unit dose" denotes the discrete form of administration, i.e. the individual tablet or capsule.

Particularly preferred according to the invention is a form of administration in which the active substance is ibandronic acid (1-hydroxy-3-(N-methyl-N-pentyl)amino-propyl-1,1-diphosphonic acid) or physiologically compatible salts thereof, e.g. the sodium salt. In accordance with the present invention, the terms physiologically compatible salt and pharmaceutically acceptable salt are interchangeable.

In order to prepare the form of administration according to the invention, the components in the bowl are mixed. The active substance, preferably together with a conventional binder such as starch paste or polyvinyl pyrrolidone K25, and optionally with addition of pharmaceutically acceptable additives and adjuvants (excipients of the inner phase), is granulated wet, preferably with water. The wet granulate is then dried and screened.

The outer phase is then added to the granulate. Either the components of the outer phase (stearic acid and adjuvant(s)), are first mixed together and added to the granulate in a further step, or the stearic acid and any other adjuvant(s) in the outer phase are added individually and directly to the granulate. The inner phase comprises about at least 80% (particularly preferred 85%) of the total weight of the dosage form, and the outer phase comprises from about 0.1% to about 20% (particularly preferred 15%) of the total weight of the dosage form.

The pharmaceutical compositions of the present invention can be processed according to conventional techniques to produce solid unit dosage forms, for example, tablets, chewing tablets, effervescent tablets, film tablets, dragees and pellets or filled into hard gelatine capsules or sachets. The mixture according to the invention can easily be processed using automatic equipment and then compressed to form tablets or filled into conventional gelatine capsules. Tablets so prepared may be coated with conventional films such as described, e.g., in WO 97/39755.

Accordingly, the invention also relates to a process for producing a solid pharmaceutical form of administration in which the active substance is a diphosphonic acid or a physiologically compatible salt thereof, wherein the active substance is processed by known methods with pharmaceutical adjuvants to obtain a granulate, less than 5% by weight of stearic acid lubricant is added to the resulting inner phase, and optionally further adjuvants are added to the mixture and the mixture is filled into capsules or compressed to form tablets.

The tablets and capsule sizes are preferably so chosen as to give an amount of active substance of 0.25–100 mg per unit dose. This determines the size of the form of administration according to the invention, depending on the biological potency of the active substances and any adjuvants capable of increasing it.

The forms of administration produced according to the invention, containing less than 5% by weight stearic acid in the outer phase, result in free-flowing, pourable compositions and do not adhere to the moulds or tools when compressed or filled into capsules.

In comparative tests using magnesium stearate lubricant in identical quantities in the outer phase, an in vitro release rate of 56% was found after 30 minutes. If these capsules were additionally heat-stressed at 40–50° C. in a drying cupboard for several weeks and the rate of release was measured again, the 30-minute value fell to below 30%.

The invention will be additionally described in the following examples without being limited thereto.

COMPARATIVE EXAMPLE 1

Production of 5.0 mg capsules containing 1.8% by weight magnesium stearate lubricant.

| Item | Composition | (mg/capsule) |
|---|---|---|
| 1 | Na-Ibandronate, monohydrate | 5.63 |
| 2 | Lactose 200 (D80) | 19.37 |
| 3 | Lactose D30 | 249.00 |
| 4 | Polyvinyl pyrrolidone K25 | 9.00 |
| 5 | Lactose D30 | 128.00 |
| 6 | Polyvinyl pyrrolidone, cross-linked | 25.00 |
| 7 | Magnesium stearate | 8.00 |
| | Weight | 444.00 |

The amount of active substance is equivalent to 5.0 mg free acid.

Processing:

A preliminary mixture was made from the active substance (Item 1) and lactose 200 (Item 2). The preliminary mixture was then wet granulated with additional adjuvants such as lactose D30 (Item 3), using polyvinyl pyrrolidone binder (Item 4). Additional lactose (Item 5) was then mixed with the granulate after drying and screening. The additives for the outer phase (Items 6 and 7) were then added individually to the mixture.

The resulting substance was filled into capsules in suitable machines. The capsules were tested as part of in-process control and immediately after production had an in vitro release rate of 56% after 30 minutes. The release rate was determined by the Paddle method after the USP.

COMPARATIVE EXAMPLE 2

Production of 5.0 mg capsules containing 0.91% by weight magnesium stearate lubricant.

| Item | Composition | (mg/capsule) |
|---|---|---|
| 1 | Na-Ibandronate, monohydrate | 5.63 |
| 2 | Lactose D80 | 19.37 |
| 3 | Lactose D30 | 249.00 |
| 4 | Polyvinyl pyrrolidone K25 | 9.00 |
| 5 | Lactose D30 | 128.00 |
| 6 | Polyvinyl pyrrolidone, cross-linked | 25.00 |
| 7 | Magnesium stearate | 4.00 |
| | Weight | 440.00 |

The amount of active substance is equivalent to 5.0 mg free acid.

The capsules were produced as in Comparative Example 1.

The result for in vitro release after 30 minutes was 56%.

The capsules in Comparative Examples 1 and 2 were heat-stressed at 50° C. in a drying oven for a number of weeks, after which the release rate was determined again. This fell to a 30-minute value below 30%.

EXAMPLE 1

Production of 5.0 mg capsules according to the invention containing a) 0.9 and b) 1.8% by weight stearic acid lubricant.

| Item | Composition | a)(mg/capsule) | b)(mg/capsule) |
|---|---|---|---|
| 1 | Na-Ibandronate, monohydrate | 5.63 | 5.63 |
| 2 | Lactose D80 | 19.37 | 19.37 |
| 3 | Lactose D30 | 249.00 | 249.00 |
| 4 | Polyvinyl pyrrolidone K25 | 9.00 | 9.00 |
| 5 | Lactose D30 | 128.00 | 128.00 |
| 6 | Polyvinyl pyrrolidone, cross-linked | 25.00 | 25.00 |
| 7 | Stearic acid | (0.9%) 4.00 | (1.8%) 8.00 |
| | Weight | 440.00 | 444.00 |

The amount of active substance is equivalent to 5.0 mg free acid.

The capsule-filling material was produced as in Comparative Examples 1 and 2. As in these Examples, the additives 6 and 7 constituted the outer phase.

After drying and screening, the material was filled into size 0 capsules.

The result for in vitro release after 30 minutes was 90% for the batch containing 4.0 mg stearic acid and 101% for the batch containing 8.0 mg stearic acid.

The capsules in the present Example 1 were also heat-stressed at 50° C. in a drying oven for a number of weeks. The rates of dissolution were then determined and were the same as before heat-stressing.

EXAMPLE 2

Production of 20 mg tablets according to the invention containing 2.5% by weight stearic acid lubricant.

| Item | Composition | (mg/tablet) |
|---|---|---|
| 1 | Na-Ibandronate | 21.38 |
| 2 | Lactose D30 | 45.52 |
| 3 | Hydroxypropyl methyl cellulose | 2.00 |
| 4 | Cellulose, microcrystalline | 3.00 |
| 5 | Polyvinyl pyrrolidone, cross-linked | 5.50 |
| 6 | Stearic acid | (2.5%) 2.00 |
| | Weight | 79.40 |

The amount of active substance is equivalent to 20.0 mg of free acid.

Processing:

The active substance was mixed with the adjuvants (Items 2, 3 and 4) and wet granulated with water. A mixture constituting the outer phase (Items 5 and 6) was added to the granulate after drying and screening. The material ready for compressing was then compressed to form tablets.

The resulting tablets were tested for the in vitro release rate immediately after production. The value after 30 minutes was 102%.

EXAMPLE 3

Production of 50 mg tablets according to the invention containing 2.5% by weight stearic acid lubricant.

| Item | Composition | (mg/tablet) |
|---|---|---|
| 1 | Na-Ibandronate | 53.45 |
| 2 | Lactose D30 | 113.80 |
| 3 | Hydroxypropyl methyl cellulose | 5.00 |
| 4 | Cellulose, microcrystalline | 7.50 |
| 5 | Polyvinyl pyrrolidone, cross-linked | 13.75 |
| 6 | Stearic acid | (2.5%) 5.00 |
| | Weight | 198.50 |

The amount of active substance is equivalent to 50.0 mg of free acid.

Processing:

The active substance was mixed with the adjuvants (Items 2, 3 and 4) and wet granulated with water. The constituents of the outer phase (Items 5 and 6) were individually mixed with the granulate after drying and screening. The material ready for pressing was then compressed to form tablets.

During tests on stability at various temperatures up to 40° C., the rate of release was repeatedly determined after various time intervals. Even after 26 weeks at temperatures of 40° C., there were no observable differences from the original rate of release.

EXAMPLE 4

Production of ibandronate 1.0 mg tablets after granulation in a fluidised bed (batch size for 60.000 tablets).

| Item | Composition | g |
|---|---|---|
| 1 | Na-Ibandronate | 64.14 |
| 2 | Lactose | 4405.86 |
| 3 | Polyvinyl pyrrolidone | 150.00 |
| 4 | Cellulose, microcrystalline | 900.00 |
| 5 | Polyvinyl pyrrolidone, cross-linked | 300.00 |
| 6 | Stearic acid | 120.00 |
| 7 | Colloidal SiO$_2$ | 60.0 |

Lactose and 600 g microcrystalline cellulose were granulated with an aqueous solution of polyvinyl pyrrolidone and ibandronate in a fluidised-bed granulator (Aeromatic type). The wet granulate was dried in the fluidised bed (Aeromatic type), passed through a 1.0 mm screen, mixed with disintegrant, lubricant, flow-regulator and 300 g microcrystalline cellulose (Turbula-type mixer, mixing time 10 minutes) and converted into tablets in a tableting press (Korsch type) having a capacity of 60,000 tablets per hour.

The amount of active substance per tablet is equivalent to 1.0 mg of free acid.

EXAMPLE 5

Production of ibandronate 2.5 mg film coated tablets after granulation in a fluidised bed

| Item | Composition | mg/coated tablet |
|---|---|---|
| 1 | Na-Ibandronate monohydrate | 2.813 |
| 2 | Lactose monohydrate | 71.687 |
| 3 | Polyvinyl pyrrolidone | 2.500 |
| 4 | Cellulose, microcrystalline | 15.000 |
| 5 | Polyvinyl pyrrolidone, cross-linked | 5.000 |
| 6 | Stearic acid | 2.000 |
| 7 | Colloidal SiO$_2$ | 1.000 |
| | Core Weight | 100.000 |
| 8 | Coating material (dry weight) | 4.000 |
| | Total Weight | 104.000 |

The amount of active substance per tablet is equivalent to 2.5 mg of free acid.

Lactose and a part (⅔) of the microcrystalline cellulose were granulated with an aqueous solution of polyvinyl pyrrolidone and ibandronate in a fluidised-bed granulator (Aeromatic type). The wet granulate was dried in the fluidised bed (Aeromatic type), passed through a screen, mixed with disintegrant, lubricant, flow-regulator and the rest of the microcrystalline cellulose and converted into tablets in a tableting press.

EXAMPLE 6

Production of ibandronate 20 mg film coated tablets after granulation in a fluidised bed

| Item | Composition | mg/coated tablet |
|---|---|---|
| 1 | Na-Ibandronate monohydrate | 22.500 |
| 2 | Lactose monohydrate | 52.000 |
| 3 | Polyvinyl pyrrolidone | 2.500 |
| 4 | Cellulose, microcrystalline | 15.000 |
| 5 | Polyvinyl pyrrolidone, cross-linked | 5.000 |
| 6 | Stearic acid | 2.000 |
| 7 | Colloidal SiO$_2$ | 1.000 |
| | Core Weight | 100.000 |
| 8 | Coating material (dry weight) | 4.000 |
| | Total Weight | 104.000 |

The amount of active substance per tablet is equivalent to 20 mg of free acid.

Lactose, a part (⅔) of the microcrystalline cellulose and ibandronate were granulated with an aqueous solution of polyvinyl pyrrolidone in a fluidised-bed granulator (Aeromatic type). The wet granulate was dried in the fluidised bed (Aeromatic type), passed through a screen, mixed with disintegrant, lubricant, flow-regulator and the rest of the microcrystalline cellulose and converted into tablets in a tableting press and coated using conventional equipment.

What is claimed is:

1. A process for producing a pharmaceutical composition in solid unit dosage form comprising granulating a binder and a ibandronic acid, a physiologically compatible salt thereof or hydrate and one or more pharmaceutically acceptable additives with water to form a granulate, the ibandronic acid being present in the dosage form in an amount of from about 0.2% to 30% by weight of the dosage form, wherein an inner phase comprises about 80% by weight of the dosage form and an outer phase comprises from about 0.1% to about 20% by weight of the dosage form;

mixing the granulate with less that about 5% stearic acid to form a mixture having the inner phase and the outer phase wherein the inner phase of the mixture contains stearic acid in an amount of about less that 5% by weight of said mixture; and forming a solid unit dosage form from said mixture.

2. A process according to claim 1, wherein at least one adjuvant is added to the stearic acid prior to mixing the stearic acid with the granulate.

3. A process according to claim 1, wherein the outer phase of the mixture includes at least one adjuvant wherein the adjuvant is added individually to the granulate.

4. A process according to claim 1, wherein at least one adjuvant is granulated with the binder and diphosphonic acid or physiologically compatible salt, said adjuvant being selected from the group consisting of lactose, starch, glucose, mannitol, microcrystalline cellulose, hydroxypropyl methyl cellulose and polyvinyl pyrrolidone.

* * * * *